Figure 1:
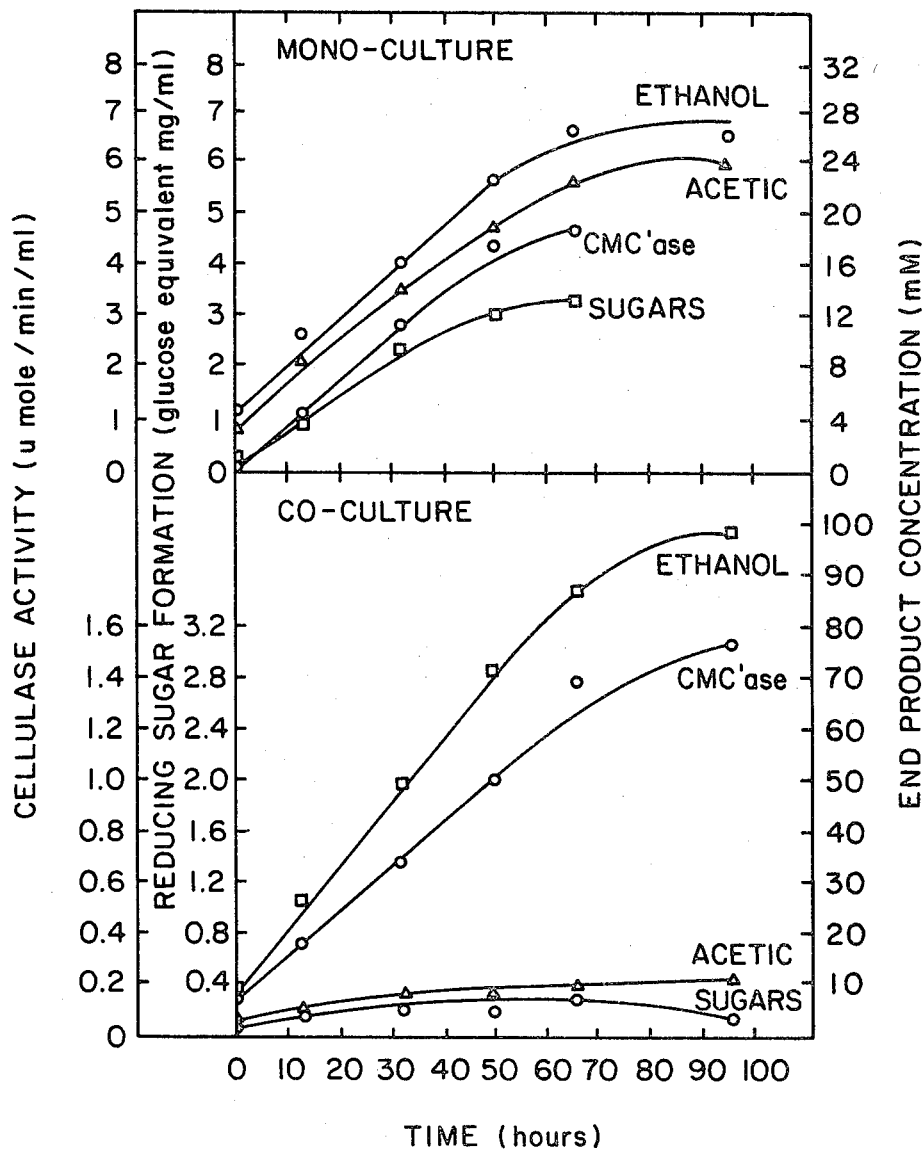

United States Patent [19]

Zeikus et al.

[11] 4,400,470
[45] Aug. 23, 1983

[54] USE OF CO-CULTURES IN THE PRODUCTION OF ETHANOL BY THE FERMENTATION OF BIOMASS

[75] Inventors: Joseph G. Zeikus, Madison, Wis.; Thomas K. Ng, Arvada, Colo.; Arie Ben-Bassat, Richmond, Calif.; Raphael J. Lamed, Rehovot, Israel

[73] Assignee: Wisconsin Alumni Research Foundation, Madison, Wis.

[21] Appl. No.: 225,093

[22] Filed: Jan. 14, 1981

[51] Int. Cl.[3] .......................... C12P 7/14; C12P 7/08; C12P 7/10; C12R 1/145

[52] U.S. Cl. .................................... 435/162; 435/163; 435/165; 435/842

[58] Field of Search ............... 435/161, 162, 163, 165, 435/170, 183, 209, 842, 99

[56] References Cited

U.S. PATENT DOCUMENTS 4,292,406 9/1981 Ljungdahl et al. ................. 435/165
4,326,032 4/1982 Grove ................................. 435/163

OTHER PUBLICATIONS

Wiegel et al., "Isolation from Soil and Properties of the Extreme Thermophile *Clostridium thermohydrosulfuricum*;" J. of Bacteriology, Sep. 1979, pp. 800–810.

*Primary Examiner*—Raymond N. Jones
*Assistant Examiner*—Elizabeth J. Curtin
*Attorney, Agent, or Firm*—McDougall, Hersh & Scott

[57] ABSTRACT

Production of ethanol and enzymes by fermentation of biomass with co-cultures of *C. thermocellum* and *C. thermohydrosulfuricum*.

5 Claims, 2 Drawing Figures

USE OF CO-CULTURES IN THE PRODUCTION OF ETHANOL BY THE FERMENTATION OF BIOMASS

The Government has rights in this invention pursuant to Grant No. PFR-7910084 and IPA No. 0001 awarded by the National Science Foundation.

This invention relates to the direct fermentation of plant cellulose and hemi-cellulose to ethanol and commercial enzymes by co-cultures of thermophilic anaerobic bacteria.

The cost and lesser availability of petroleum and natural gas has generated research interest in bio-conversion processes that makes use of renewable biomass resources for the production of fuels and chemical feed stocks. Anaerobic fermentations have formed the basis for such microbial chemical and fuel production. By catabolizing organic matter in the absence of oxygen, a variety of reduced organic compounds such as ethanol, methane, acetic acid, lactic acid and the like have been produced in lieu of complete aerobic combustion of such organic matters to $CO_2$ and $H_2O$.

Several factors account for the technological interest in thermophilic bacterial fermentation as opposed to mesophilic yeast and/or bacteria. Bacterial fermentation enables direct conversion of the cellulosic and hemi-cellulosic components of preferred delignified biomass to chemicals or fuels, without pretreatment to depolymerize the substrates. As a consequence of growth at high temperatures and unique macromolecular properties, obligately thermophilic bacteria can possess high metabolic rates, physically and chemically stable enzymes, and a higher end product to cell ratio than in metabolically similar mesophilic species. Thermophilic processes are more stable, rapid, and facilitate reactant activity and product recovery. Fermentation of biomass at temperatures above 60° C. is limited to thermophilic bacteria.

These features of thermophilic bacterial systems are important for the development of viable biotechnology. Important is the fact that thermophilic fermentations may lower the energy requirements for recovery of volatile products, such as enabling reduced pressure distillation from a fermenter operating under vacuum conditions. Ethanol producing thermophiles, with rapid metabolic rates, are especially desirable from the standpoint of self heating and novel methods for product recovery.

It is an object of this invention to provide a method for the production of ethanol in high yield and purity by fermentation of plant cellulosic and hemi-cellulosic materials with thermophilic and anaerobic bacteria.

Relatively little is known about the entire spectrum of thermophilic anaerobic bacteria as applied to bio-fuel and bio-chemical production. A fundamental approach for development of the desired bio-conversion technology has been adopted by way of examination of the microorganisms in pure and in co-cultures to define their metabolism, especially in terms of defining key rate limiting and regulatory factors of catabolism.

These investigations have led to the discovery that ethanol production in high yield can be achieved with strains that utilize the α and hemi-cellulose components in plant cellulose or biomass and by the use of strains that produce ethanol in high yields. It has been found that such high conversion ratio of cellulose to ethanol can be achieved in a single stage fermentation when use is made of co-cultures of *Clostridium thermocellum* and *Clostridium thermohydrosulfuricum* in the fermentation process.

These two thermophilic anaerobic bacteria differ one from the other in many respects. Comparison of their growth properties are tabulated in the following Table 1, using *C. thermocellum* LQRI and *C. thermohydrosulfuricum* 39E as representative. From the table it will be apparent that the growth properties of these two species differed significantly. The optimum temperature for growth of *C. thermocellum* and *C. thermohydrosulfuricum* were 62° C. and 65° C. respectively. *C. thermocellum* fermented cellulose, cellodextrins and glucose as energy sources, whereas *C. thermohydrosulfuricum* fermented a variety of hexoses and pentoses but not cellulose. Significant is the fact that *C. thermocellum* LQRI did not ferment pentoses or hemi-cellulose. *C. thermohydrosulfuricum* displayed a faster growth rate on glucose than did *C. thermocellum* and the growth of the latter was almost three times more rapid on cellobiose than on cellulose.

TABLE 1

Growth Characteristics of *C. thermocellum* LQRI and *C. thermohydrosulfuricum* 39E

| Conditions | LQRI | 39E |
| --- | --- | --- |
| Temperature range for growth: | | |
| Min. | −40° C. | 40° C. |
| Opt. | 62° C. | 65° C. |
| Max. | <70° C. | 75° C. |
| Substrates supporting growth | cellulose cellodextrins cellobiose glucose | pyruvate glucose cellobiose xylose mannose fructose starch |
| Substrates not supporting growth | fructose xylose mannose starch pyruvate | cellodextrins cellulose xylan mannan |
| Growth rate on: | | |
| glucose | 0.44 hr$^{-1}$ | 0.78 hr$^{-1}$ |
| cellobiose | 0.5 hr$^{-1}$ | 0.67 hr$^{-1}$ |
| cellulose | 0.15 hr$^{-1}$ | — |

Comparison between the end products of glucose and cellobiose fermentation of *C. thermohydrosulfuricum* and *C. thermocellum* give further indication of the vast differences between the two microorganisms. As shown in Table 2, both species produced the same fermentation products which include $H_2$, $CO_2$, acetic acid, ethanol, and lactic acid, but in drastically different proportions. Most significantly, the ethanol to acetate ratio of *C. thermohydrosulfuricum* was 18 as compared to 1.2 for *C. thermocellum*. Similar ethanol to acetate ratios were observed when these two strains grew on substrates other than cellobiose or glucose. The yield of ethanol per mole of glucose equiv. fermented by *C. thermohydrosulfuricum* (1.84) approximated the maximum yield for ethanol fermentation; whereas, a value of 0.8 was observed for *C. thermocellum*. Also worth noting, *C. thermohydrosulfuricum* produced lower amounts of $H_2$ than *C. thermocellum*. *C. thermohydrosulfuricum* strain 39E produced the highest yield of ethanol of any other described thermophilic saccharolytic anaerobe.

TABLE 2

Fermentation Products of *C. thermocellum* LQRI and *C. thermohydrosulfuricum* 39E

|  | LQRI | 39E |
|---|---|---|
| Substrate consumed | 131 μmoles cellobiose | 298 μmoles glucose |
| Products formed | Total μmoles | |
| $H_2$ | 275 | 31 |
| $CO_2$ | 340 | 580 |
| Ethanol | 207 | 549 |
| Acetic | 170 | 31 |
| Lactic | 46 | 50 |
| Ethanol/glucose equivalent (mole/mole) | 0.79 | 1.84 |
| Ethanol/acetate (mole/mole) | 1.22 | 17.71 |

Since such vast differences have been found to exist in the growth and fermentation characteristics of *C. thermocellum* and *C. thermohydrosulfuricum*, it was indeed unexpected to find that co-cultures formed of these two species gave conversion ratios of plant cellulose (i.e. α and hemi-cellulose) to ethanol which far exceeded the ratios obtainable from either species alone. A synergism is clearly indicated by the co-culture, especially when employed in the conversion of plant cellulose to ethanol.

This has been demonstrated by the fermentation of several substrates by mono- and co-cultures of *C. thermocellum* in the absence or presence of *C. thermohydrosulfuricum*. The experimental conditions under which the comparisons were carried out comprised the use of anaerobic tubes filled with 10 ml of GS medium and 0.7% by weight substrate. Fermentation was carried out at 62° C. Amounts of substrate degraded after 120 hours were 100% (MN300 cellulose) and 80% (Solka Floc cellulose). Delignified wood was also fermented to ethanol. The delignified wood was aspen wood chemically delignified with $SO_2$ or treated by steam exploding poplar wood. The results are set forth in Table 3 and Table 4. Ethanol and acetic acid production and CMCase activity were examined in cultures growing on MN300, Solka Floc, chemically delignified wood or untreated wood. Under these conditions, mono- and co-cultures degraded (>80%) Solka Floc and MN300, degraded 50% of delignified wood but did not significantly metabolize the untreated wood even after 168 hours of incubation. The ethanol to acetate ratio in the co-culture was greater than three times higher than in the mono-culture. Similarly, the yield of ethanol per mole of glucose equiv. metabolized was 100% higher in co-culture as opposed to mono-culture. Reducing sugars were in much lower amounts in the co-culture at the termination of the fermentation.

TABLE 3

Comparison of cellulose fermentation in a mono-culture of *C. thermocellum* LQRI and a co-culture of *C. thermocellum* LQRI and *C. thermohydrosulfuricum* 39E

| Substrate | Culture | Products formed Ethanol (μmol) | Acetate (μmol) | Ethanol/ Acetate (mole/mole) | Ethanol/ Glu. Equiv. (mole/mole) | Carboxymethyl Cellulase (IU/mg) |
|---|---|---|---|---|---|---|
| MN300 Cellulose | Mono | 316 | 264 | 1.2 | 0.81 | 3.30 |
|  | Co | 688 | 45 | 15.4 | 1.77 | 1.31 |
| Solka Floc | Mono | 317 | 225 | 1.4 | 0.81 | 2.66 |
|  | Co | 703 | 37 | 19.3 | 1.81 | 1.02 |
| Delignified Aspen Wood | Mono | 171 | 156 | 1.1 | 0.88 | — |
|  | Co | 323 | 144 | 2.3 | 1.66 | — |
| Aspen Wood | Mono | 6 | 27 | 0.2 | — | — |
| Control | Co | 26 | 38 | 0.7 | — | — |

Experimental conditions: Anaerobic tubes contained 10 ml of modified GS medium and 0.7% substrate. Amounts of substrate degraded were 90% (after 48–96 hrs), 50% (after 168 hrs) and <1% (after 168 hrs) respectively for cellulosic substrates, delignified wood and wood. Aspen wood was chemically delignified by $SO_2$ treatment.

TABLE 4

Comparison of fermentations of cellulosics by a mono-culture of *C. thermocellum* LQRI and a co-culture of *C. thermocellum* and *C. thermohydrosulfuricum*[a]

| Substrate | Condition | Products Formed (mM) Ethanol | Acetate | CMCase (U/ml) | Reducing Sugar (mg/ml) | Substrate Consumed (%) | Ethanol/Acetate Ratio (mol/mol) |
|---|---|---|---|---|---|---|---|
| MN300 | Mono- | 31.2 | 22.5 | 2.66 | 1.28 | 60 | 1.39 |
|  | Co- | 88.9 | 4.2 | 0.79 | 0.08 | 100 | 21.1 |
| Solka Floc | Mono- | 30.8 | 27.3 | 4.61 | 2.89 | 50 | 1.13 |
|  | Co- | 98.7 | 11.3 | 1.54 | .15 | 80 | 8.73 |
| $SO_2$—Treated Wood | Mono- | 16.9 | 13.6 | 2.14 | 1.55 | — | 1.24 |
|  | Co- | 54.3 | 11.2 | 1.0 | .64 | — | 4.85 |
| Steam Exploded Wood | Mono- | 14.9 | 15.2 | 2.97 | 1.58 | — | 0.98 |
|  | Co- | 63.9 | 6.6 | 0.72 | 0.12 | — | 9.68 |
| Untreated Wood (control) | Mono- | 2.2 | 6.4 | — | — | — | 0.34 |
|  | Co- | 8.4 | 9.3 | — | — | — | 0.90 |

[a]Experiments were performed in anaerobic culture tubes that contained 10 ml of GS medium and 1.0% substrate except for MN300 cellulose (0.8%). Tubes were incubated without shaking at 62° C. for 120 h.

FIG. 1 shows the kinetics of product formation during Solka Floc cellulose fermentation in *C. thermocellum* mono-culture and in co-cultures with *C. thermohydrosulfuricans*. Solka floc is a wood cellulose that contains both cellulose and hemicellulose. Ethanol, acetate, cellulase and reducing sugars were formed by the co-culture but at drastically different rates than that observed in mono-culture. Reducing sugar accumulation in the co-culture was 10 fold lower than in the mono-culture. At 1% Solka floc the accumulated sugars consisted mainly of xylobiose, lower amounts of glucose and xylose, and only traces of cellobiose. Carboxymethycellulase (CMCase) was produced during the fermentation but the rate of production was three times lower in the co-culture than the mono-culture. Despite the lower production of CMCase, the co-culture fermented cellulose (as measured by residual cellulose) at similar rates to that of *C. thermocellum* alone. Most importantly the rate of ethanol production in co-culture increased three fold; whereas acetate production ceased early in the fermentation (~30 h) and the final acetate concentration was >2 times less than that of the mono-culture. The co-culture was very stable at 62°, repeatably transferable, and contained approximately equal numbers of each species. Essentially the same high ethanol production rates and yields were obtained in *C. thermohydrosulfuricum* mono-culture fermentation of Solka Floc cellulose that contained cellulase from *C. thermocellum*. Several physiological and biochemical properties of *C. thermocellum* and *C. thermohydrosulfuricum* help explain the basis for enhanced fermentation of Solka floc cellulose to ethanol in co-culture. These features include: the ability of *C. thermocellum* cellulase to degrade $\beta(1,4)$-xylan, or glycans; the ability of *C. thermohydrosulfuricum* to ferment xylose and xylobiose and to incorporate cellobiose and glucose faster than *C. thermocellum;* and a lower proton concentration associated with fermentation of equivalent amounts of cellulose by the co-culture.

Several thermostable enzymes were obtained from the cellulose fermenting co-culture that displayed high rates of catalysis.

The following Table 5 compares the properties of the enzymes that were obtained.

TABLE 5

Activity and Stability of Enzymes Recovered from the Cellulose Fermentating Co-culture

|  | Thermal stability | $Q_{10}$ | Specific Activity ($\mu$moles/min/mg protein at 60 C. |
|---|---|---|---|
| Extracellular cellulase | 70 C. | 1.57 (30° C.–70° C.) | 0.42[a] |
| Cell-bound Reversible NADP linked Alcohol dehydrogenase | 86 C. | 1.9 (>50° C.) 2.9 (<50° C.) | 1.6 |
| Cell-bound Malic Enzyme | 65 C. | 2.1 (22° C.–60° C.) | 6.70 |

[a]Specific activity is expressed in $\mu$moles of carbohydrate/min/mg protein, and determined by the continuous spectrophotometric assay for the quantification of cellulase solubilizing activity.

The cellulase was easily recovered from the culture supernatant by a variety of common precipitation procedures. The cellulase was stable, active at 70° C. and devoid of proteolytic activity. The high cellulose solubilizing activity of the crude enzyme was not affected by oxygen. Enzymes were easily extracted from the cell pellet including the reversible NADP linked alcohol dehydrogenase of *C. thermohydrosulfuricum* and the malic enzyme of *C. thermocellum*. Both of these enzymes displayed high thermostability and activity, and were present in catabolic amounts.

These data indicate that the direct fermentation of cellulose to ethanol and commercial enzymes by co-cultures of *C. thermocellum* and *C. thermohydrosulfuricum* has utility as a biological system for biomass conversion. The ethanol yield during cellulose hydrolysis by *C. thermocellum* was increased 100% in co-culture with *C. thermohydrosulfuricum* which rapidly metabolizes mono- and disaccharides of hexose and pentose. Active, thermal stable enzymes produced by the co-culture that are of potential industrial and/or analytical value included: supernatant cellulase and cell-bound alcohol dehydrogenases and malic enzyme.

It will be apparent from the foregoing that co-cultures of different species provide for efficient conversion of plant biomass to ethanol. Higher ratios and yields of ethanol are obtainable from these co-cultures as compared to mono-cultures and co-culture fermentations have been found to be more stable from the corresponding mono-cultures. From regulation studies in thermophilic saccharolytic bacteria, it appears that for higher ethanol ratios and yield, the presence of exogenous electron acceptors should be avoided in the fermentation. Hydrogen pressure should be kept sufficiently high to enhance ethanol formation and to inhibit hydrogen and acetate formation. For increased ethanol production, it is desirable to make use of co-cultures with high saccharide to ethanol conversion rates that use both hemi-cellulose and cellulose, i.e. hexose and pentose derivatives, are important in biomass fermentation.

The co-culture data suggests that the rate and yield of ethanol production from cellulose was increased as a result of more effective uptake of cellulase hydrolytic products than by increasing the specific activities of cellulase. The rate of cellulolysis as a rate-limiting step can be improved for process development, as well as the rate of uptake of hydrolysis products by *C. thermocellum*. While this may be achieved by genetic manipulation of *C. thermocellum*, it is preferably achieved by the use of the described co-culture technique.

It has been found that the inhibition of acetaldehyde reductase by low NAD concentration gives a higher level of acetate production in *C. thermocellum* as opposed to *C. thermohydrosulfuricum*. High alcohol concentration (e.g. >1%) also decreased the rate of ethanol production by the alcohol dehydrogenases of both *C. thermocellum* and *C. thermohydrosulfuricum*. Thus, mutants of both species can be used to increase the rate and yield of ethanol production from cellulose as a result of derepressing alcohol dehydrogenase activity by genetic manipulations.

Figure 2:
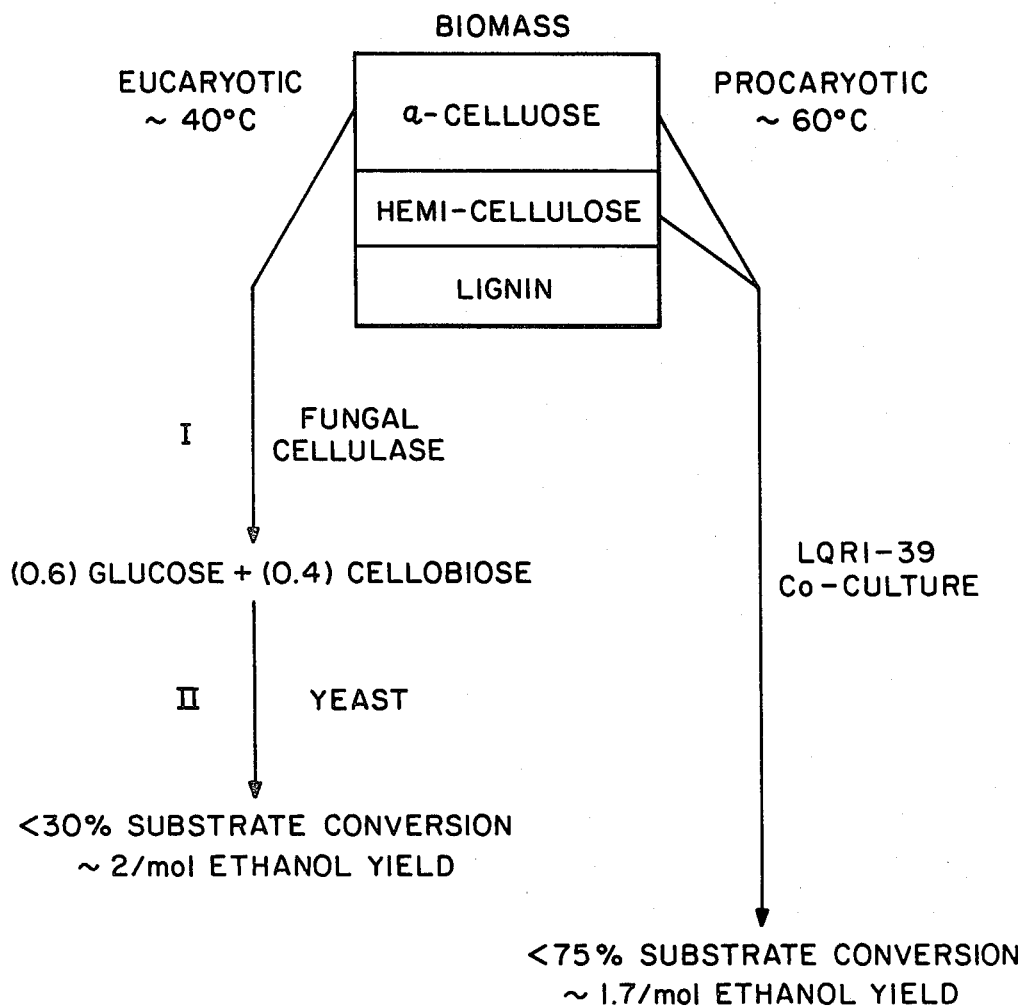

Thermophilic ethanol fermentations are of interest to industrial alcohol production because both the pentosic and hexosic fraction of biomass can be directly fermented in high yield (i.e. mol ethanol/mol substrate consumed), and because of potential novel process features associated with high temperature operation. As a net result, the co-culture cellulose fermentations described here have the potential to convert more substrate to alcohol than other bioconversion systems as shown in FIG. 2.

Therefore, having described the invention process and product it is understood that mutants of both species can be used without departing from the invention as set forth in the following claims.

What is claimed is:

1. In the method of producing ethanol and enzymes as a by-product of ethanol production by the fermentation of biomass, the improvement comprising subjecting the biomass which includes cellulose and hemi-cellulose containing plant materials to fermentation under thermophilic conditions in the presence of co-cultures of *Clostridium thermocellum* and *Clostridium thermohydrosulfuricum*, the ratio of the cultures being in an amount whereby the conversion ratios of cellulose:e- thanol and hemi-cellulose:ethanol are greater than the ratios obtained by use of either Clostridium species alone.

2. In the method of producing ethanol and enzymes as a by-product of ethanol production by the fermentation of biomass, the improvement comprising subjecting the biomass which includes cellulose and hemi-cellulose containing plant materials to fermentation by *Clostridium thermohydrosulfuricum* under thermophilic conditions in the presence of the elaborated enzymes produced by *Clostridium thermocellum*, the ratio of the *Clostridium thermohydrosulfuricum* to the elaborated enzymes being in an amount whereby the conversion ratios of cellulose:ethanol and hemi-cellulose:ethanol are greater than the ratios obtained by use of either Clostridium species alone.

3. The method as claimed in claim 1 in which the fermentation is carried out at a temperature of about 60°–65° C.

4. The method as claimed in claims 1 or 2 in which the enzymes produced comprise extra cellular cellulase, cell bound reversible NADP linked alcohol dehydrogenase and cell bound malic enzyme.

5. The method as claimed in claims 1 or 2 in which the fermentation is carried out anaerobically in the presence of hydrogen maintained at a pressure sufficient to promote ethanol formation but inhibit hydrogen and acetate formation.

* * * * *